United States Patent [19]
Hatch et al.

[11] Patent Number: 6,001,260
[45] Date of Patent: Dec. 14, 1999

[54] COLLAPSIBLE APPARATUS FOR COMPRESSING PACKING MATERIAL IN LIQUID CHROMATOGRAPHY COLUMNS AND METHODS OF USE

[75] Inventors: Richard G. Hatch, Berkeley; Chiko Fan, Danville, both of Calif.

[73] Assignee: Varian Associates, Inc., Palo Alto, Calif.

[21] Appl. No.: 08/868,252

[22] Filed: Jun. 3, 1997

Related U.S. Application Data

[62] Division of application No. 08/609,967, Feb. 29, 1996, Pat. No. 5,667,675.

[51] Int. Cl.$^6$ .................................................. B01D 15/08
[52] U.S. Cl. ....................................... 210/656; 210/198.2
[58] Field of Search .................................... 210/635, 656, 210/659, 189, 198.2, 241, 268, 456; 95/82; 96/101; 141/12.73, 80; 422/70

[56] References Cited

U.S. PATENT DOCUMENTS

| | | | |
|---|---|---|---|
| 3,935,884 | 2/1976 | Hazelton | 141/80 |
| 3,966,609 | 6/1976 | Godbile et al. | 210/198.2 |
| 4,549,584 | 10/1985 | Morin et al. | 141/73 |
| 4,597,866 | 7/1986 | Couillard | 210/198.2 |
| 4,892,654 | 1/1990 | Nickerson | 210/198.2 |
| 4,927,531 | 5/1990 | Sakamoto | 210/198.2 |
| 5,013,446 | 5/1991 | Li | 210/198.2 |
| 5,141,635 | 8/1992 | Le Plang | 210/198.2 |
| 5,158,676 | 10/1992 | Kreher et al. | 210/198.2 |
| 5,167,809 | 12/1992 | Mann | 210/198.2 |
| 5,169,522 | 12/1992 | Shalon | 210/198.2 |
| 5,192,433 | 3/1993 | Shalon | 210/198.2 |
| 5,213,683 | 5/1993 | Mann | 210/198.2 |
| 5,378,359 | 1/1995 | Huse | 210/198.2 |
| 5,462,659 | 10/1995 | Saxena | 210/198.2 |

OTHER PUBLICATIONS

PROCHROM Manufacturers of Liquid Chromatography (HPLC) Units, Nov. 1995, Chemical Equipment, pp. 20 and 54.

PROCHROM Laboratory Scale Preparative High Performance Liquid Chromotagraphy, pp. 1–12, Jul. '93.

IBF Biotechnics "High Performance Preparative Liquid Chromatography" 2 page catalog insert, (undated).

1992 "EM Separations", Chromatography catalog, pp. 51–53, 1992.

E. Merck, Jan. 1989, "Merck Spectrum". pp. 54 and 55.

*Primary Examiner*—Ernest G. Therkorn
*Attorney, Agent, or Firm*—Robert R. Meads

[57] ABSTRACT

Longitudinally collapsible apparatus for compacting packing material within a tubular liquid chromatography column. The apparatus includes a first support member, a second support member and a movable support member. The movable support member is releasably connectable to the second support member for support thereby. When released from the second support member, the movable member is adapted to ride on guide members extending between the first and second support members. A compression mechanism is supported on the movable support member to move therewith to a longitudinally collapsed position for the apparatus. The compression mechanism comprises a reversible drive for an axially movable rod carrying a movable piston. With the movable support member secured to the second support member, the piston of the compression mechanism is movable in an end of the tubular column when the column is supported on the first support member. Movement of the movable piston within the column axially compresses a column packing material as the piston is driven towards an opposite end of the column. The piston also is releasably connectable to the tubular column to raise and lower the column when the apparatus extends in a vertical direction and is it is desired to insert an end piston into or remove the end piston from the opposite end of the column or when it is desired to change an adapter ring on the first support member to receive a column of a different diameter for packing by the apparatus.

2 Claims, 10 Drawing Sheets

COLLAPSIBLE APPARATUS FOR COMPRESSING PACKING MATERIAL IN LIQUID CHROMATOGRAPHY COLUMNS AND METHODS OF USE

RELATED APPLICATION

This Application is a division of U.S. patent application Ser. No. 08/609,976 filed Feb. 29,1996, now U.S. Pat. No. 5,667,675.

BACKGROUND

Liquid chromatography is a commonly used means of purification for complex chemical mixtures, a practice generally known as preparative chromatography. In preparative chromatography, a fluid known as the mobile phase is passed under pressure, through a compact bed of particulate material known as the stationary phase. The material to be separated into constituent components, known as the sample, is passed through the stationary phase by means of the mobile phase and is separated into its components by means of differential interaction with the stationary phase. For the effective use of preparative chromatography, it is essential that the bed of stationary phase be prepared as a compact bed of high uniformity.

Most preparative chromatography is performed in tubular metal columns of 2, 4 or 6 inch or larger diameter. Preparation of such large diameter columns is difficult using conventional slurry packing wherein a suspension of stationary phase is forced or "packed" into a chromatographic column using a high pressure stream of liquid to produce a homogeneous and stable column structure. Rather, today, the preferred method of preparing large diameter columns for use in preparative chromatography is the method commonly referred to as "axial compression". Axial compression is described in U.S. Pat. Nos. 3,966,609 and 5,169,522. In the '609 patent a piston containing a filter matrix and fluid sealing mechanism is used to compact a bed of stationary phase and maintain adequate compression to correct column instability. In the '522patent a compression ram is used to consolidate the stationary phase during the packing operation.

While the axial compression method of U.S. Pat. No. 3,966,609 does produce highly efficient preparative columns which are stabilized against failure due to stationary phase compaction, the method and apparatus described in the patent do not permit the nondestructive removal of packed columns from the compressive means if it is desired to pack a new column. Thus, packing a new column requires either an additional compression equipment, or the existing column must be destroyed. Similar disadvantages exist for equipment that uses a fluid powered hydraulic compression mechanism that is operated as an integral part of the separation column, as seen in U.S. Pat. Nos. 4,597,866 and 5,169,522. In such equipment, complex compression mechanisms must be fabricated for each separation column produced, thereby adding additional expense.

While a modification of the apparatus of U.S. Pat. Nos. 3,966,609 and 5,169,522, as shown in U.S. Pat. No. 4,549,584, permits packed columns to be removed from the compressive equipment, additional potentially damaging operations such as trimming or shaping of the stationary phase bed and attachment of end fittings are required to finish the preparation of the columns. Further, the finished columns are thereafter not amenable to use in axial compression equipment because of use of fixed end plates as end fittings.

A modification of the column packing apparatus of the U.S. Pat. No. 4,549,804 is embodied in the axial self compression preparative cartridge columns of IBF Biotechnics, Inc., of Savage, Maryland. The IBF apparatus permits the removal of packed column units from the compression mechanism of the apparatus so that the separation column may be a simple modular component. Also, the apparatus may be used to compress packing materials in other columns when mounted in the apparatus. However, because the apparatus holds the column within a tightly fitted housing, such compression of packing materials in other columns is limited to columns of the same diameter as the original column.

Prepbar separation systems manufactured by E. Merck of Darmstadt Germany, are designed to compress packing material in columns of different diameter; such systems providing for the packing, compression, and operation of modular columns of various diameters using the same compression mechanism. However, the columns designed for use in the Merck system require complex flange type column closures to allow connection of the high pressure tubing used to apply and collect the material to be separated and the mobile phase. These flange type connections add unnecessary complexity to the apparatus. In addition, no simple means is provided for the removal of spent packing material from the Merck separation columns after use.

Another problem associated with all prior column packing apparatus employing axial compression is a lack of portability the need to provide for an adequate length of compression. Such length of compression generally approximates the length of column being packed plus the length for the compression mechanism such as a hydraulic cylinder. For columns of adequate length for efficient chromatographic use, the combined length can easily exceed 2 meters, which creates problems in shipping and portability for the end users. In shipping, the equipment must generally be disassembled, which creates a need for heavy and cumbersome parts to be reassembled at the intended location of use. A similar problem results if the user desires to move the equipment from one location to another, since many doorways or passageways are not high enough to pass such a tall apparatus.

Some column packing equipment, such as the "Dan Process" manufactured by A/S Gentofte, Denmark is designed to provide reduced height by rotation of some of its components, so the length is directed horizontally. Since large diameter preparative chromatography equipment is generally composed of heavy metal parts and tubes, such rotation of components may be dangerous because of the momentum associated with swinging parts of large mass. Furthermore, changing the direction of some components to a horizontal direction may solve the height problem for moving the equipment, but it may cause other problems if, for example, the equipment must be transported by elevator or around tight corners.

Thus, there is a need for liquid chromatography column packing apparatus which is simple, vertically collapsible and which is useable with columns of a variety of diameters. The present invention satisfies such needs.

SUMMARY OF INVENTION

The present invention provides apparatus for producing and operating highly efficient preparative columns while avoiding the disadvantages of the prior art. In the present invention, a tubular column or column tube is provided with end closures containing filters capable of retaining the stationary phase and provisions for the introduction and removal of liquid under pressure. The end closures, generally known as bed supports, are supported within opposite ends of the column tube against outward axial motion by piston elements which provide both fluid connections for the passage of mobile phase and high pressure sealing elements to prevent leakage of the mobile phase from the column. At least one of the bed supports and its supporting piston are movable within the column tube and are subjected by means of a compression mechanism to a compressive force larger than that generated by the pressure drop occurring from the passage of liquid through the stationary phase. The compressive force permits the preparation and continued operation of high performance liquid chromatographic columns.

In a typical embodiment of the invention, the compressive mechanism comprises a hydraulic press including a vertically extending hydraulic cylinder containing a compression rod supporting a compression piston at its lower end. The compression piston functions as the upper support piston for the column tube containing packing material to be compressed by the apparatus of the present invention. The cylinder is mounted on a movable support member which is mounted for vertical movement on vertical guide members extending between upper and lower support members. The lower support member is designed to support the column tube containing packing material which is to be compressed. The movable support member is designed for releasable connection to the upper support member. When the movable member is released from the upper support member it is movable downward to vertically collapse the apparatus of the present invention. When the movable support member is connected to the upper support member, the compression piston is movable axially into an upper open end of the column tube which is vertically mounted on the lower support member. Upon actuation of the compression mechanism, the compression rod is driven downward to drive the compression piston into the column tube to engage an upper bed support and to compact the packing material within the column tube against a lower bed support and a stationary lower piston within a lower end of the column tube. The compression piston and the lower stationary piston include annular fluid seals for sealing with an inner surface of the column tube and contain fluid passages for the introduction and removal of mobile phase. The lower support member is provided with an opening through which spent packing may be extruded. This opening is reduced in diameter for packing and operation by the mounting of an adapter plate or ring. The adapter ring may be selected from a variety of diameters to permit the operation of columns of different diameters using the same compression mechanism.

To prepare a liquid chromatography column using the apparatus of the present invention, the correct size adapter ring is mounted on the lower support member. The lower piston and bed support are then mounted on the lower support member via the adapter ring, and the column tube is pressed downward onto the lower bed support and lower piston to close the lower end of the column tube. A suspension of stationary phase is introduced into the upper end column tube, which is then closed by the upper bed support. At least one of the bed support-piston sets is provided with a connection for liquid to exit the apparatus during processing. The upper movable bed support is then subjected to a compressive force by the compression piston, which causes the movable bed support to travel downward within the column tube in an axial direction until excess slurry solvent is expelled and the stationary phase is compacted. The column is then ready for operation and may be connected to a liquid chromatographic system for use. There is no need for additional processing operations and the column is suitable for additional compression, unlike those prepared in accordance with U.S. Pat. No. 4,549,584.

In the present invention, the stationary phase in the column is operated under compression by the movable upper piston. However, both the upper and lower pistons can be removed from the column tube without removing the bed supports. Since there is no need to remove the movable bed supports from the column tube, there is reduced danger of damage to the stationary phase structure from removal of the pistons. The compression mechanism and pistons can then be used to prepare additional columns without destroying the columns previously prepared using the compression mechanism. Also, columns previously prepared using the compression mechanism may be recompressed and again operated under compression to maintain column performance.

It is a further feature of the present invention that the use of interchangeable adapter plates or rings and piston sets permits the use of the compression mechanism with columns of differing diameters without encumbering each column with complex and costly flanges or other devices to connect to fluid flow passages. This allows column tubes according to the present invention to be of simple design and constitutes an advantage over previous designs.

After the use of chromatographic column of the present invention is complete, the spent stationary phase is easily removed from the column by raising the column tube, removing the lower piston, lowering the column tube and using the compression mechanism to extrude the stationary phase through the opening in the lower support member. The bed supports are easily removed by the same extrusion. The use of the adapter plates and lower piston provides for this simple extrusion process, which is not present in the Merck system.

In the present invention, the hydraulic press is adapted to two further uses beyond the compression of the stationary phase for operation or extrusion. First, the hydraulic press is used to raise and lower the column tube during the operations of inserting the lower bed support and piston, and during the removal of the piston before stationary phase extrusion. Since large diameter column tubes can weigh more than 50 pounds even when empty, such use of the hydraulic press provides a significant advantage to the operator. The operator need only mount the column tube on the lower support of the apparatus. All subsequent lifting and lowering is performed by the apparatus itself. In particular, such column raising and lowering is accomplished by coupling the upper end of the column tube so that the tube follows the motion of the compression rod. The coupling can be performed using a number of methods. The preferred method is by using a removable pin which passes through a hole through the column tube and the piston at a right angle to the tube axis.

In another significant improvement associated with the present invention, the hydraulic press is used to allow the collapsing of the compression mechanism in a vertical dimension. In this regard, the guide members connecting the upper and lower support members are provided with bearings to allow linear motion of the movable support member. When it desired to collapse the apparatus for relocation, shipping or storage, the column tube is first removed. The compression rod of the hydraulic press is then fully extended so that it rests against an adaptor plate which blocks the opening in the lower support member. With the actuator and movable support now supported by the compression rod extending from the hydraulic press, fasteners locking the movable support member to the upper support member can be removed to permit linear motion of the movable support downward on the bearings. By retracting the compression rod of the hydraulic press, the hydraulic press and movable member can be smoothly lowered to the bottom of the guide members or even to meet the lower support. With the hydraulic press so lowered, the overall height of the apparatus is greatly reduced, e.g. by approximately 40%.

BRIEF DESCRIPTION OF DRAWINGS

FIG. 3 also depicts a front face of the control panel for controlling operation of the apparatus.

FIG. 4 shows the compression rod in a raised position to lift the column tube from the adaptor ring and lower support member, the adaptor ring shown supporting a lower piston and bed support for closing the lower open end of the column tube. The lower piston includes openings for passing liquid from the column tube during operation of the column.

DETAILED DESCRIPTION OF INVENTION

Figure 1:
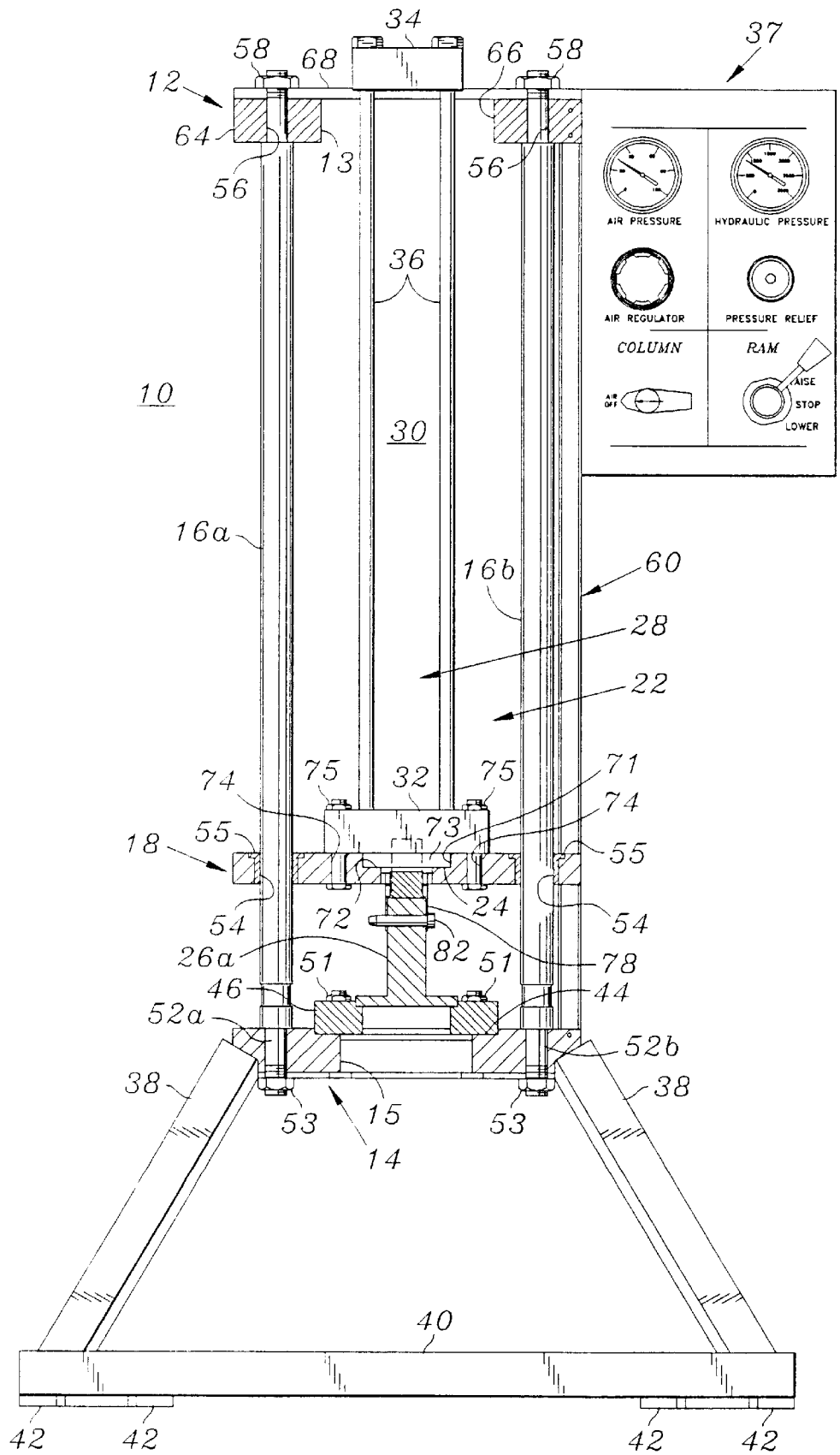
FIG. 1 is a side view partially in section of the apparatus of the present invention for compressing packing material in a liquid chromatography column. The apparatus is shown in a vertically collapsed position for ease in packaging and movement of the apparatus.

Basically, as depicted in FIGS. 1, 2, 2a, 3, 4, 5 and 6, the apparatus 10 of the present invention comprises an upper support member 12 and a lower support member 14 having central through holes 13 and 15 respectively. The lower support member 14 is separated from the upper support member 12 by four vertical guide members or rods 16a, b, c and d secured to the upper and lower support members. The guide members 16a–d provide vertically guided moveable support for a moveable support member 18 which is releaseably connectable by a connector 20 to the upper support member 12.

The apparatus 10 further comprises a column packing compression mechanism 22 comprising a compression rod 24, a compression piston 26 and a drive 28 preferably including a hydraulic cylinder 30 having lower and upper flanges 32 and 34 respectively secured by tie rods 36. The column packing compression mechanism 22 is secured to movable support member 18 for vertical movement therewith to vertically collapse 10 when the moveable support member 18 is released from the upper support member 12 as depicted in FIG. 1.

When the moveable support member 18 is secured to the upper support member 12, operation of the drive 28 by actuation of knobs on a control panel 37 cause the compression rod 24 to move vertically to raise and lower the compression piston 26 which is sized to fit snugly into an open upper end of a column tube 35 as shown in FIGS. 3, 4, 5 and 6. The column tube is supported on the lower support member 14 over the central hole 15 and downward movement of the compression piston 26 within the column tube compresses a packing material within a lower end of the column tube.

Figure 1A:
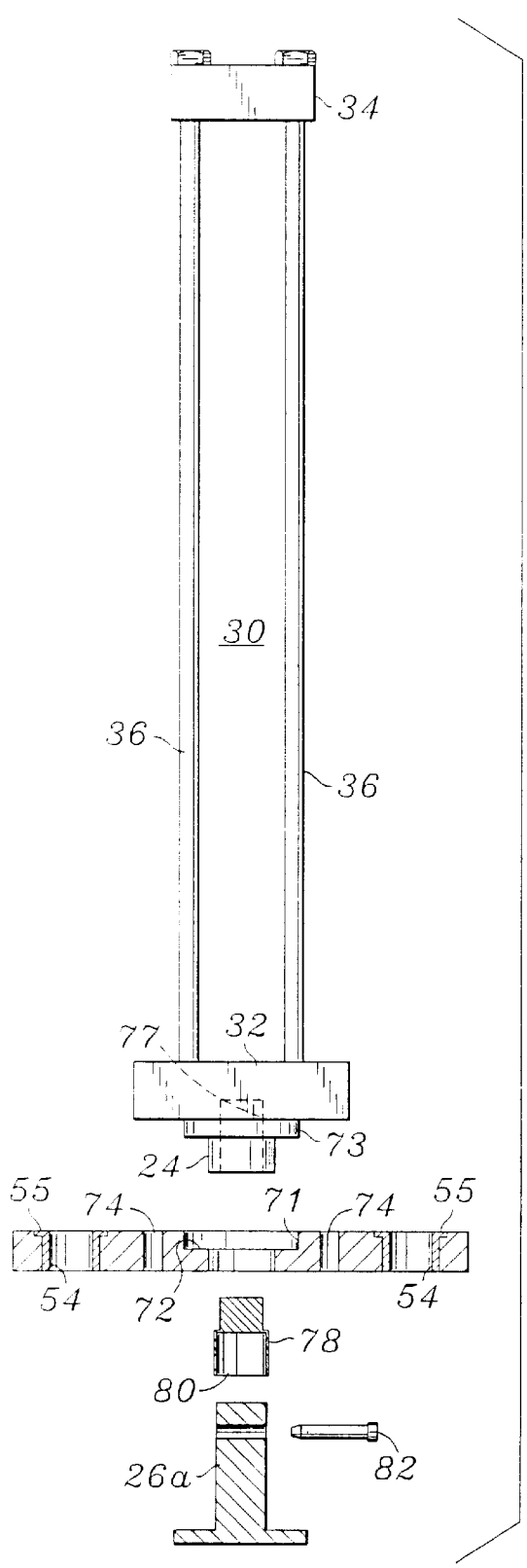
FIG. 1a is a an exploded view of a column packing compression mechanism shown in FIG. 1 illustrating the component part comprising a vertically extending compression rod, a piston at a lower end of the compression rod and a drive for vertically moving the compression rod comprising a hydraulic cylinder.
Figure 1B:
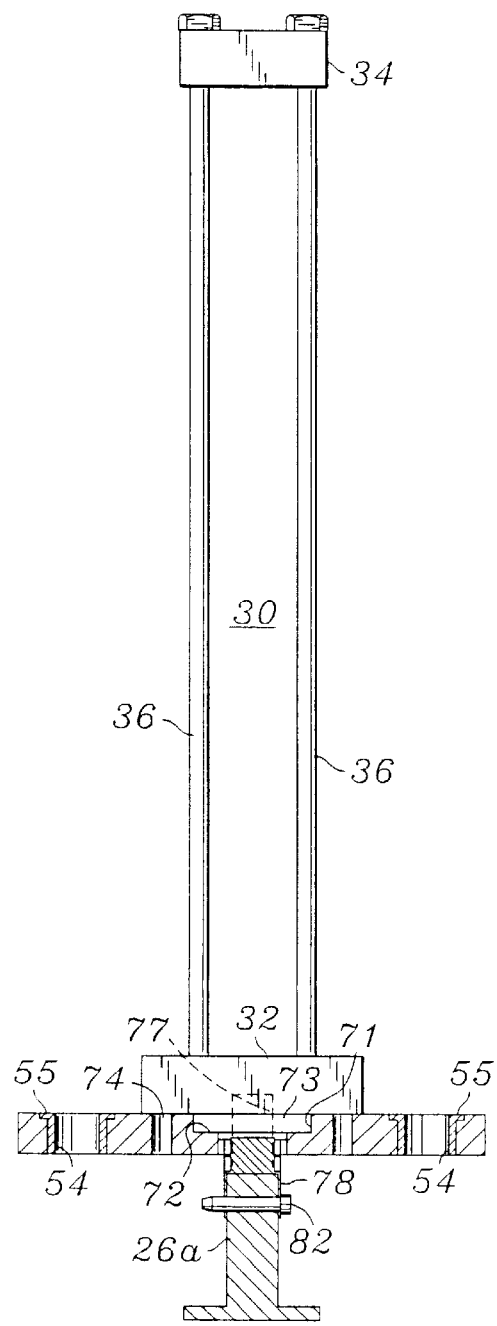
FIG. 1b is a side view showing the components in FIG. 1a assembled with the piston secured to the compression rod by a universal coupler and a laterally extending pin, the piston shown in FIGS. 1, 1a and 1b being a "dummy" piston for use when the apparatus of the present invention is to be vertically collapsed.
Figure 1C:
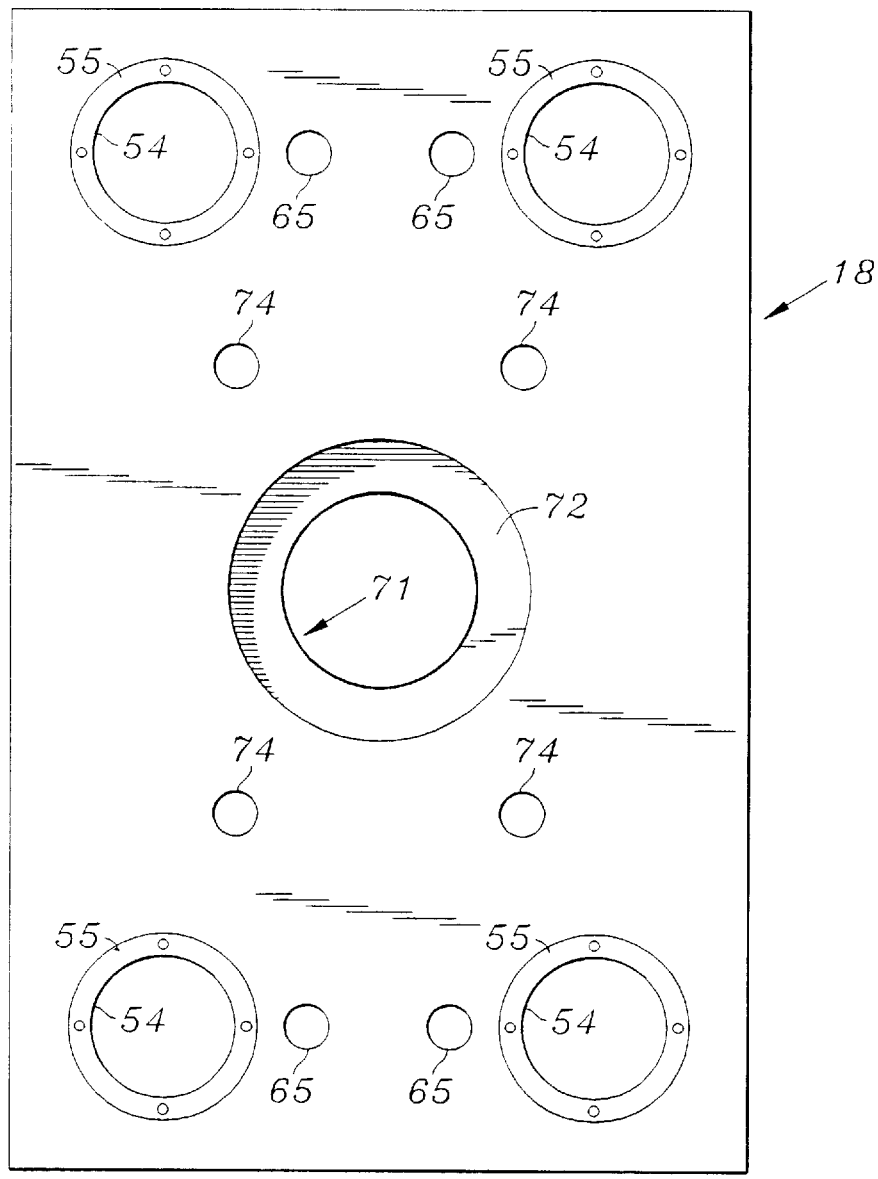
FIG. 1c is a top view of a moveable support member comprising a plate for connection to the hydraulic cylinder of the column packing compression mechanism.
Figure 1D:
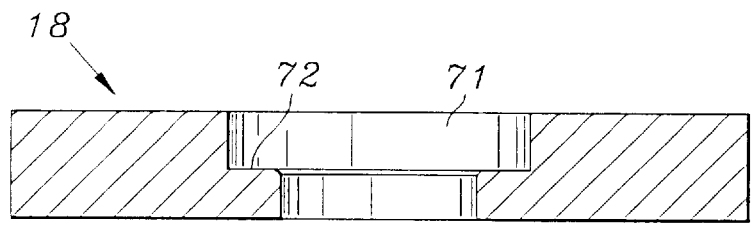
FIG. 1d is a cross sectional side view of the moveable support plate of FIG. 1c.
Figure 1E:
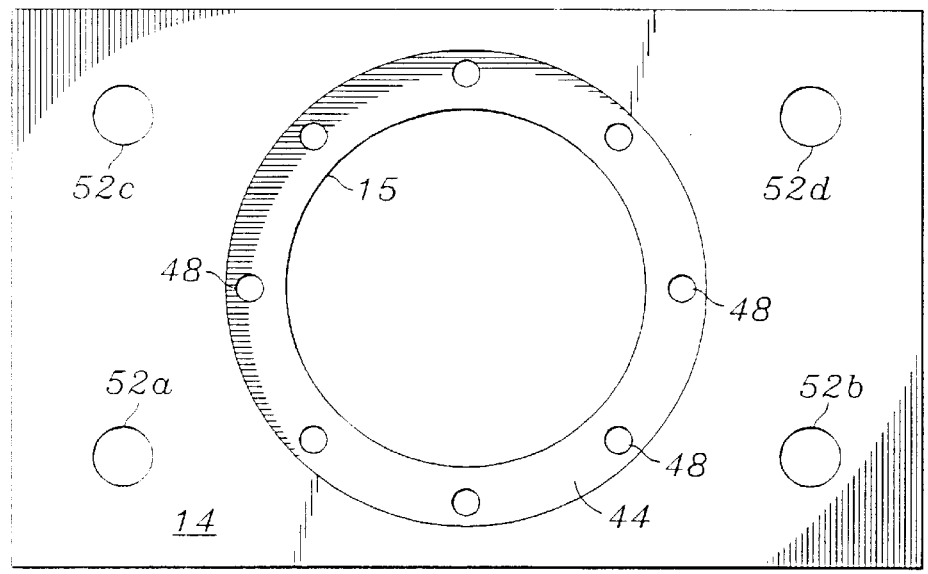
FIG. 1e is a top view of a lower support member comprising a lower support plate having a lower opening for receiving an adaptor ring.
Figure 1F:
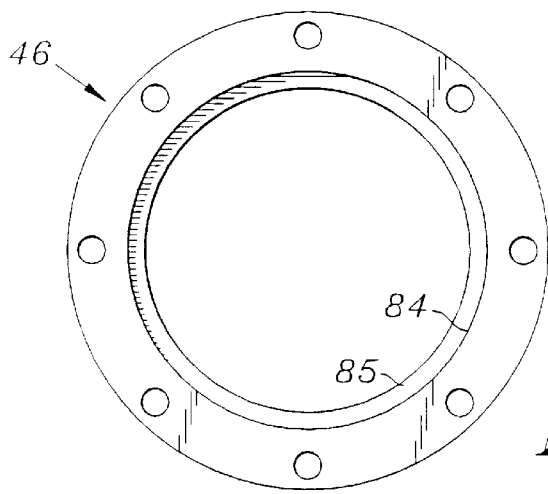
FIG. 1f is a top view of an adaptor ring for mounting on the lower plate of FIG. 1e to receive a column tube to vertically support the column tube on the lower support plate.

As depicted most clearly in FIGS. 1e and f, the lower support member 14 preferably comprises a plate secured as shown FIG. 1 at its corners to tubular legs 38 extending downwardly and outwardly for connection to a base member 40 riding on wheels 42. The plate comprising the lower support member 14 includes an annular recess 44 around the central hole 15 for receiving an adaptor ring 46 as shown in FIG. 1f. A plurality of internally threaded holes 48 circumferentially spaced in the recess 44 are designed to receive bolts 51 for releasably securing the adaptor ring 46 in the recess as shown in FIG. 1. In addition, the lower support member 14 includes four through holes 52a–d, one at each corner of the lower support member vertically receiving end portions of the guide rods 16a–d having threaded lower ends for receiving nuts 53 as shown in FIG. 1.

The lower support member 14 thus vertically supports the guide members 16a–d to extend vertically through aligned holes 54 in the moveable support member 18 and holes 56 in the upper support member where upper threaded ends are secured by nuts 58 as shown FIG. 1. The guide rods 16a–d thus vertically support the upper support member 12 above the lower support member 14.

Figure 2A:
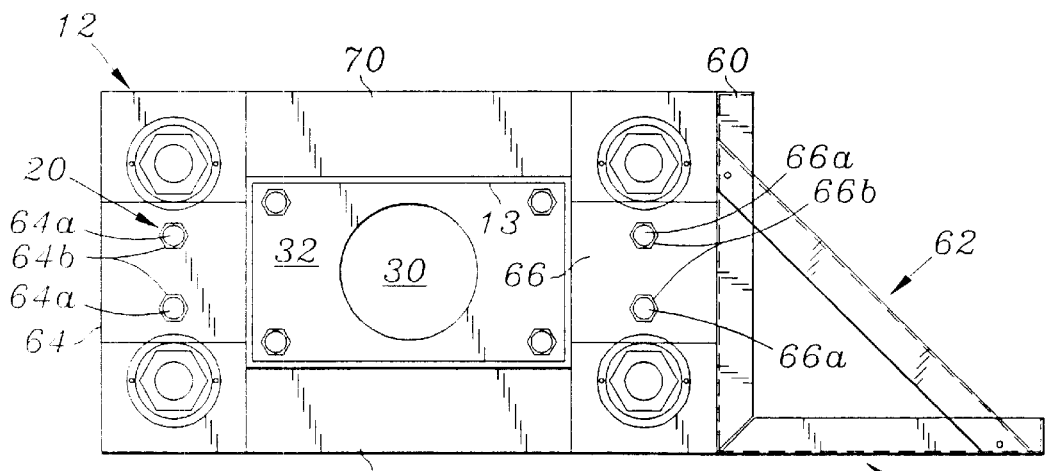
FIG. 2a is a top view of the apparatus shown in FIG. 2 depicting the upper support member and showing the moveable support member secured to the upper support member and control panel secured to a mounting bracket.

As shown in FIG. 1, the upper support member 12 also is connected to the lower support member 14 by a vertical u-channel support 60 which provides guidance for pneumatic and hydraulic control tubing extending between and secured to a right side of the upper and lower support members 12 and 14. As shown in FIG. 2a, the upper support member 12 also provides support for a mounting bracket 62 which supports the control panel 37.

As shown more particularly in FIG. 2a, the upper support member 12 comprises rearwardly extending support blocks 64 and 66 including the through holes 56 for receiving the upper end portions of the guide rods 16a–d at the four corners of the upper support member 12. As shown in FIG. 2a, cross member 68 and 70 are supported on tops of the support blocks 64 and 66 to extend there between and combine with the support blocks to define the central through hole 13 in the upper support member 12.

Figure 3:
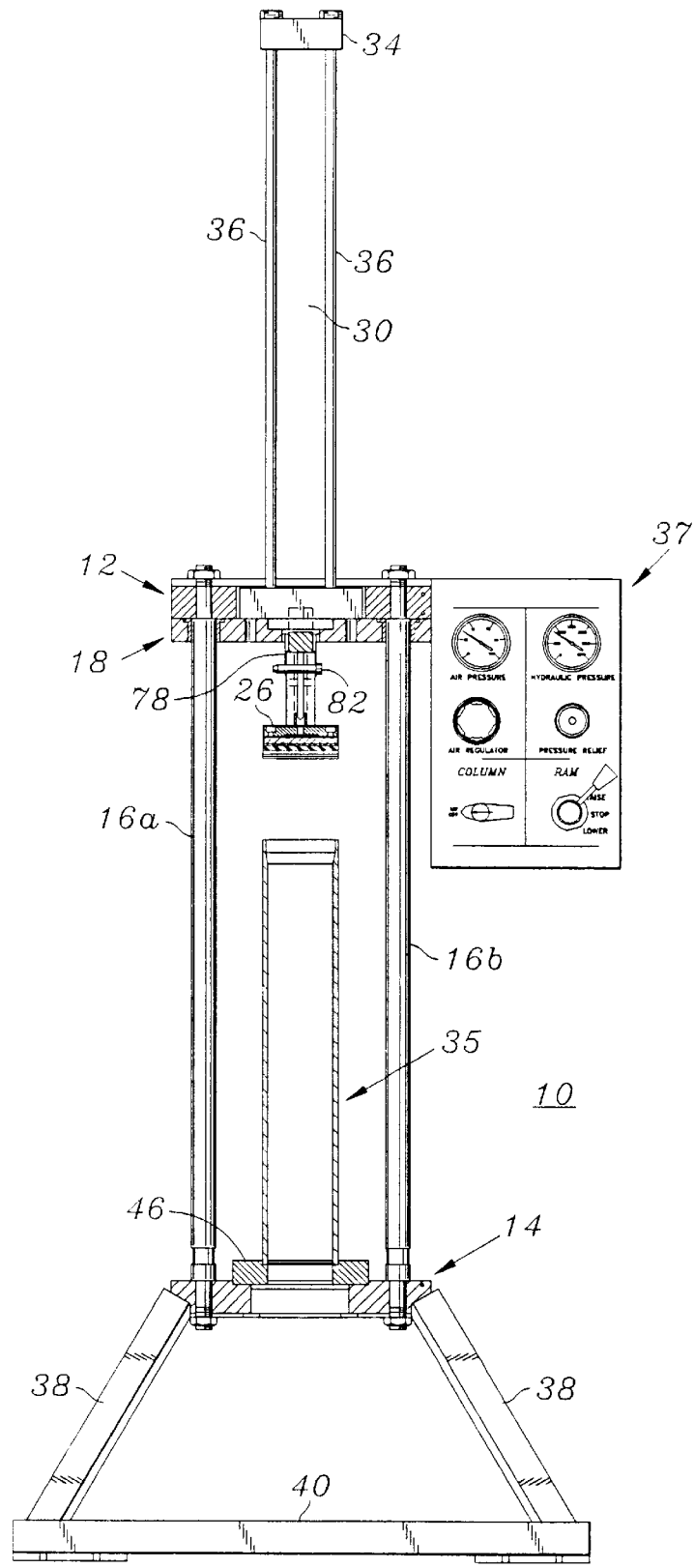
FIG. 3 is a side view partially in section showing an adaptor ring mounted on a lower support member of the apparatus and vertically supporting a column tube between the lower support member and the moveable and upper support members. The compression rod of the column packing compression mechanism is shown supporting a compression piston for fitting into an upper open end of the column tube.

As previously indicated, the upper support member 12 is adapted to secure the moveable support member 18 thereto when it is desired to operate the apparatus 10 in compressing a packing material within the column tube 35. To accommodate such connection, the support blocks 64 and 66 include through holes 64a and 66a respectively. Such holes are designed to receive vertically extending bolts 64b and 66b passing through the support blocks 64 and 66 into threaded holes 65 moveable support member 18 (see FIG. 1c) to releaseably secure the moveable support member to the upper support member 12 as shown in FIG. 2a. Thus secured to the upper support member 12, the moveable support member 18 provides vertical support for the hydraulic cylinder 30 of the column packing compression mechanism 22 above the upper support member 12 as shown in FIG. 3. In this regard, and as most clearly shown in FIGS. 1c and 1d, the moveable support member 18 comprises a flat plate including a central stepped opening 71 defining an annular shoulder 72 for receiving a lower face of a cylinder gland 73 of the hydraulic cylinder 30. Thus positioned, the lower flange 32 of the cylinder rests on the top face of the moveable support plate 18 with bolts extending through mating threaded holes 74 in the moveable support plate and lower flange 32. The threaded holes 74 receive bolts 75 to releaseably secure the flange to the moveable support plate as shown most clearly in FIG. 1. With the column packing compression mechanism 22 thus supported on the moveable support member 18 as shown in FIG. 1, the compression rod 24 extends axially from the cylinder 30 through the opening 71 in the moveable support plate 18 to releaseably secure the compression piston 26 (FIG. 3) in line with an open upper end of the column tube 35 mounted on the lower support member 14 as shown in FIG. 3. Such connection of the compression rod 24 to the compression piston 26 is most clearly depicted in FIG. 3 as well as in FIGS. 1a and 1b for a "dummy" piston connected to the compression rod 24. As there illustrated, the lower end of the compression rod 24 includes a threaded socket 77 for receiving an externally threaded upper end of a cylindrical coupler 78 to secure the coupler to the compression rod 24. The coupler 78 also include a lower socket 80 having laterally extending side holes there through. The socket 80 is dimensioned to receive the upper end of the compression piston 26 in FIG. 3 or a "dummy" piston 26a as depicted in FIGS. 1a and 1b. In both instances, the piston includes a laterally extending through hole for receiving a connecting pin 82 after the piston has been inserted upwardly into the lower socket 80 as most clearly depicted in FIGS. 1b and 3.

As previously indicated, in addition to supporting the column packing compression mechanism 22, the moveable support member 18 is adapted to ride vertically on the guide rods 16a–d between the upper support member 12 and a lower position as depicted in FIG. 1 when the apparatus 10 is in its vertically collapsed condition. To accommodate such vertical movement of the moveable support member 18, the moveable support plate as shown in FIGS. 1 and 1c include the four holes 54 each containing a sleeve bearing 55 for receiving an associated one of the guide rod 16a–d. The sleeve bearings 55 provide low friction surfaces for allowing vertical movement of the moveable support member 18 between the vertical collapsed position of the apparatus 10 as shown in FIG. 1 and the raised position of the moveable support member and its connection to the upper support member as shown in FIGS. 2, 3, 4, 5 and 6.

Figure 2:
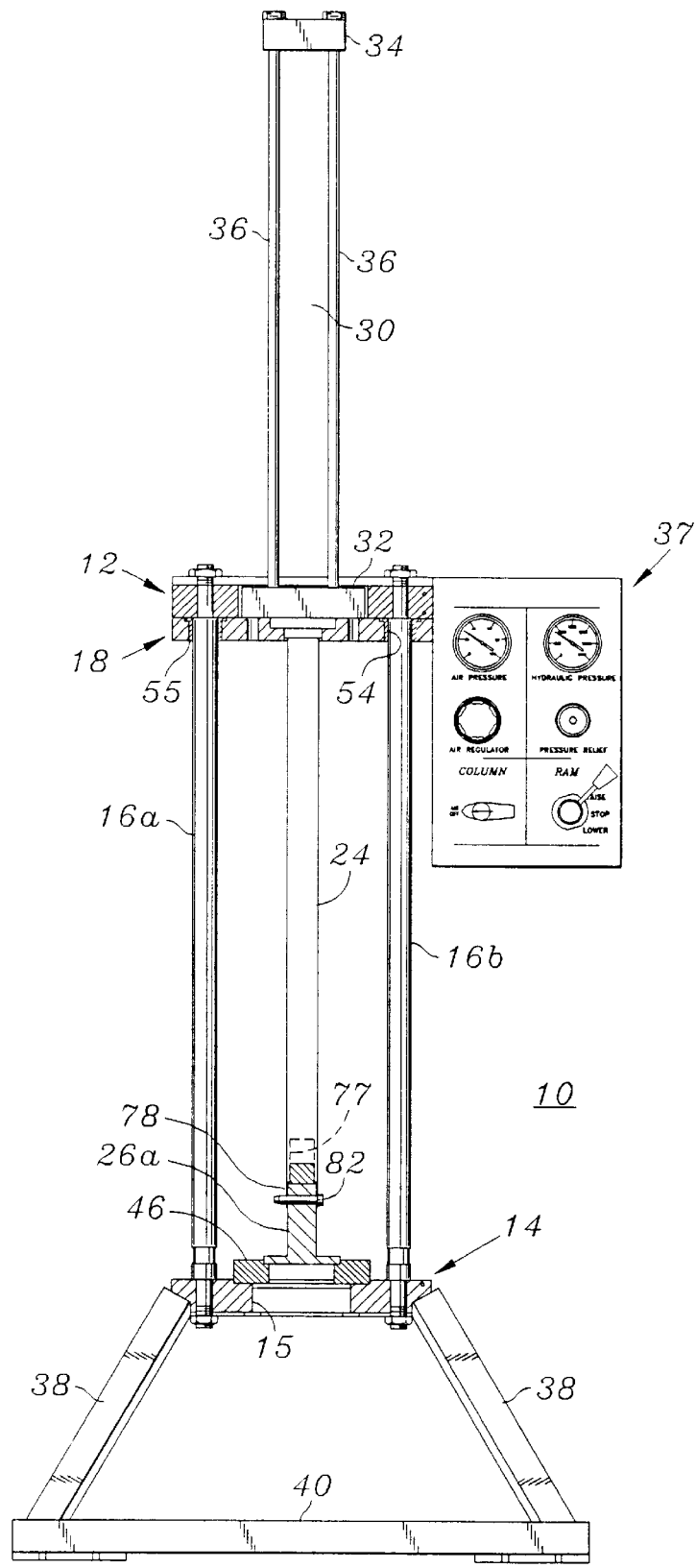
FIG. 2 is a side view partially in section of the apparatus of FIG. 1 with the moveable support plate secured to an upper support member and with the moveable support plate supporting the hydraulic cylinder in an upward extended position with a compression rod of the column packing compression mechanism and "dummy" piston bearing on the lower support member.

In the vertically collapsed position for the apparatus 10, the "dummy" piston 26a bears adaptor ring 46 mounted on the lower support member 14. In the raised position for the moveable support member 18 as depicted in FIGS. 3–6, the compression system 22 is raised from the lower support member 14 which provides vertical support for the column tube 35 containing packing material which is to be compressed upon downward movement of the compression piston 26 into the column tube. To provide such support for the "dummy" piston 26a as shown FIGS. 1 and 2 and for the column tube 35 as shown in FIGS. 3–6, the lower support plate 14 includes the previously described adaptor ring 46. As shown most clearly in FIG. 1f, the adaptor ring includes an annular recess 84 forming an annular shoulder 85 for receiving a bottom face of the "dummy" piston 26a as depicted in FIGS. 1 and 2 or the lower end of the column tube 35 as depicted in FIGS. 3–6.

As previously indicated, user control of the controls on the control panel 37 determines the operation of the apparatus 10 in moving to and from the vertically collapsed position shown in FIG. 1 and in the placement of the column tube 35 and its end closures and pistons in the ends of the column tube and the subsequent compression of a packing material within the column. To accomplish this, the column packing compression mechanism 22 as previously described preferably is a model 2H hydraulic ram manufactured by Parker-Hannifin Corp. of Des Plaines, Ill. The hydraulic ram is connected in a conventional manner and controlled by the fluid circuit depicted in FIG. 7 under control of the controls indicated on the control panel 37. In particular, the ram comprises the hydraulic cylinder 30 with the compression rod 24 extending downwardly therefrom. Fluid to control the raising and lowering of the compression rod within the cylinder is controlled by operation of a directional control valve 90 shown in FIG. 7 and on the control panel 37 in FIGS. 1, 2 and 3 through 6.

The directional valve 90 is a conventional three position valve for regulating the direction of fluid flow to and from the hydraulic cylinder 30. The hydraulic cylinder includes an internal piston for driving the compression rod 24 in and out of the hydraulic cylinder in a conventional manner. For example, with the directional control valve 90 in the position indicated, fluid flows into an upper end of the hydraulic cylinder 30 and returns from a lower end of the cylinder to drive the compression rod 24 downwardly and out of the hydraulic cylinder. When the directional control valve 90 is in its second or intermediate position, all flow of fluid to the hydraulic cylinder 30 is blocked. When the control valve is in its lower or third position, the direction of flow is reversed such that fluid flows into the lower end of the hydraulic cylinder 30 below its internal piston and exits the hydraulic cylinder at the upper end for return to the reservoir 92.

Figure 7:
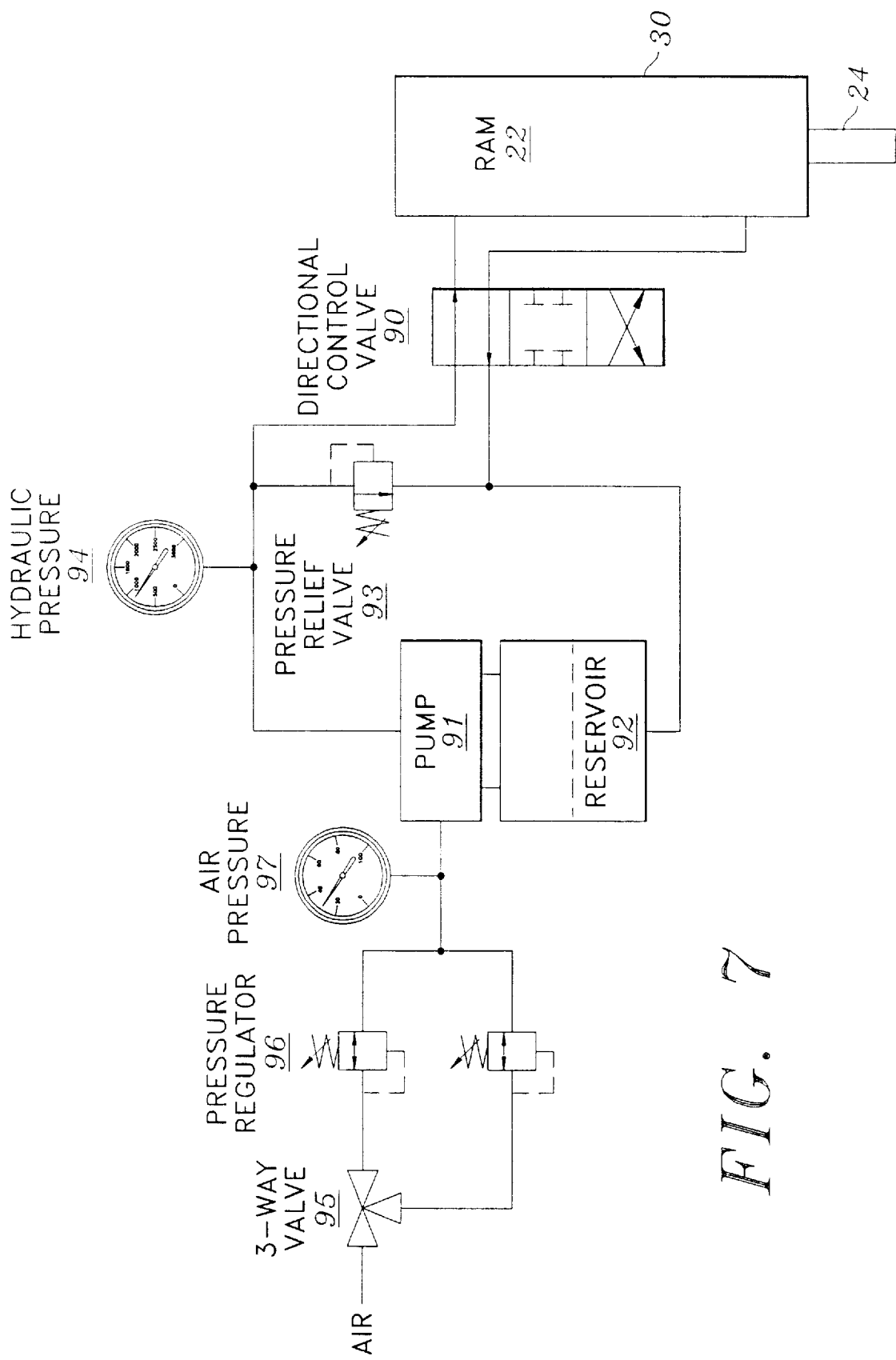
FIG. 7 is a block diagram of a hydraulic control system for the apparatus having the control panel shown in FIG. 6.

As depicted in FIG. 7, the source of fluid for driving the compression mechanism 22 is a fluid reservoir 92 for supplying fluid to a pump 91. The pump 91 is also of conventional design commonly referred to as an "air amplifier". In operation, the pump 91 draws fluid from the reservoir 92, elevates the pressure of the fluid and supplies it to the directional control valve 90 for passage to the hydraulic cylinder 30 in the manner previously described. A pressure release valve 93 regulates the fluid pressure by providing a return path to the reservoir 92 and the hydraulic pressure is monitored by a conventional hydraulic pressure gauge 94.

Operation of the air amplifier pump 91 requires a supply of air to the pump. Such a supply is indicated in FIG. 7 at "fair", which is a supply of air to a three-way valve 95. In one position, the three-way valve 95 blocks the supply of air. In a second position, the three-way valve passes air to a pressure regulator 96 on the control panel 37. In a third position, the three-way valve passes air to a preset air regulator mounted behind the control panel and inaccessible to a user. The pressure regulators are of conventional design and limit the hydraulic pressure which may be generated within the system. The air pressure is monitored by an air pressure gauge 97 on the control panel 37.

Thus, in operation air from the source of regulated pressure is delivered to the pump 91 which in operation draws and compresses fluid from the reservoir 92 for application to the directional control valve 90. Then, depending upon the setting of the directional valve 90 by an operator, the compression rod 24 is raised and lowered relative to the lower support member 14 and the column tube 35 during different operations performed by the apparatus 10.

In this regard, and as previously indicated, the apparatus 10 is susceptible as several different operations. First, as depicted in FIGS. 1 and 2, the apparatus may be vertically collapsed to reduce the vertical dimension of the apparatus to a minimum allowing for compact packaging and shipping of the apparatus as well as for movement of the apparatus from one location to another in a laboratory through doorways and the like without requiring a tilting or rotation of components of the apparatus. Such collapsing of the apparatus 10 is accomplished by removing the column tube 35 from the apparatus and with the "dummy" piston 26a attached to the lower end of the compression rod 24, setting the control knob "RAM" to the "lower" position. This results in the compression rod being driven downwardly to the position indicated in FIG. 2 with the "dummy" piston bearing on the top of the adaptor ring 46 secured to the lower support member 14. Then, upon a disconnection of the connector 20 securing the moveable support member 18 to the upper support member 12, continued operation of the hydraulic system with the RAM control in the "raise" position lowers the hydraulic cylinder 30 with the moveable support member 18 downwardly on the guide rods 16 to the lower or collapsed position shown in FIG. 1.

When it is desired to again extend the apparatus 10, the process is simply reversed. With the hydraulic cylinder 30 in the lower position shown in FIG. 1, the control knob "RAM" is switched to the "lower" position. This drives the hydraulic cylinder 30 and moveable support member 18 upwardly to the position shown in FIG. 2 where the connector 20 again releaseably locks the moveable support member to the upper support member. Continued operation of the hydraulic system then with the control knob "RAM" in the "raise" position withdraws the compression rod 24 upwardly within the hydraulic cylinder 30 to the position shown in FIG. 3 where the "dummy" piston 26a may be replaced by the compression piston 26 and the apparatus 10 readied to receive a column tube 35 as shown in FIG. 3.

Figure 4:
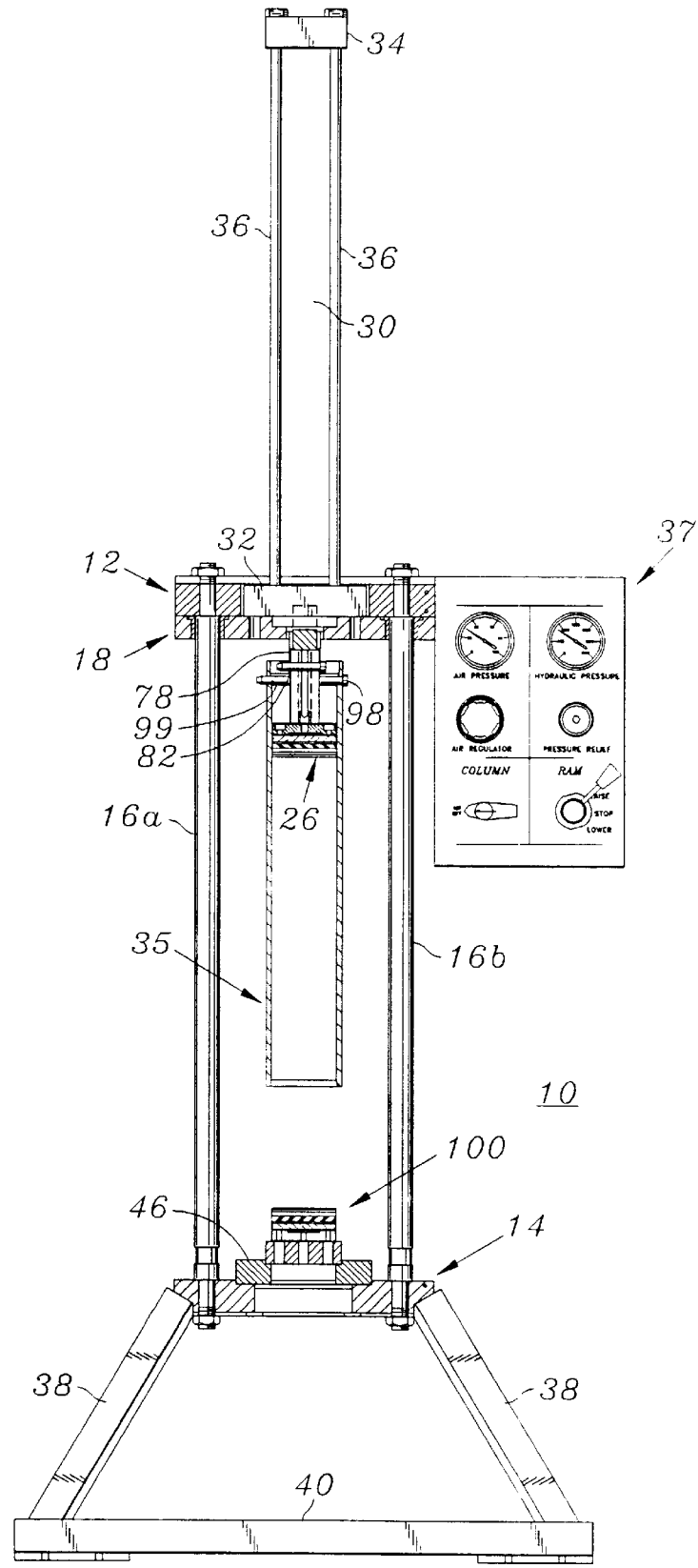
FIG. 4 is a side view partially in section similar to FIG. 3 and illustrating the compression rod and compression piston releaseably secured to the column tube by a pin extending through aligned openings in the column tube and compression rod above the compression piston.
Figure 5:
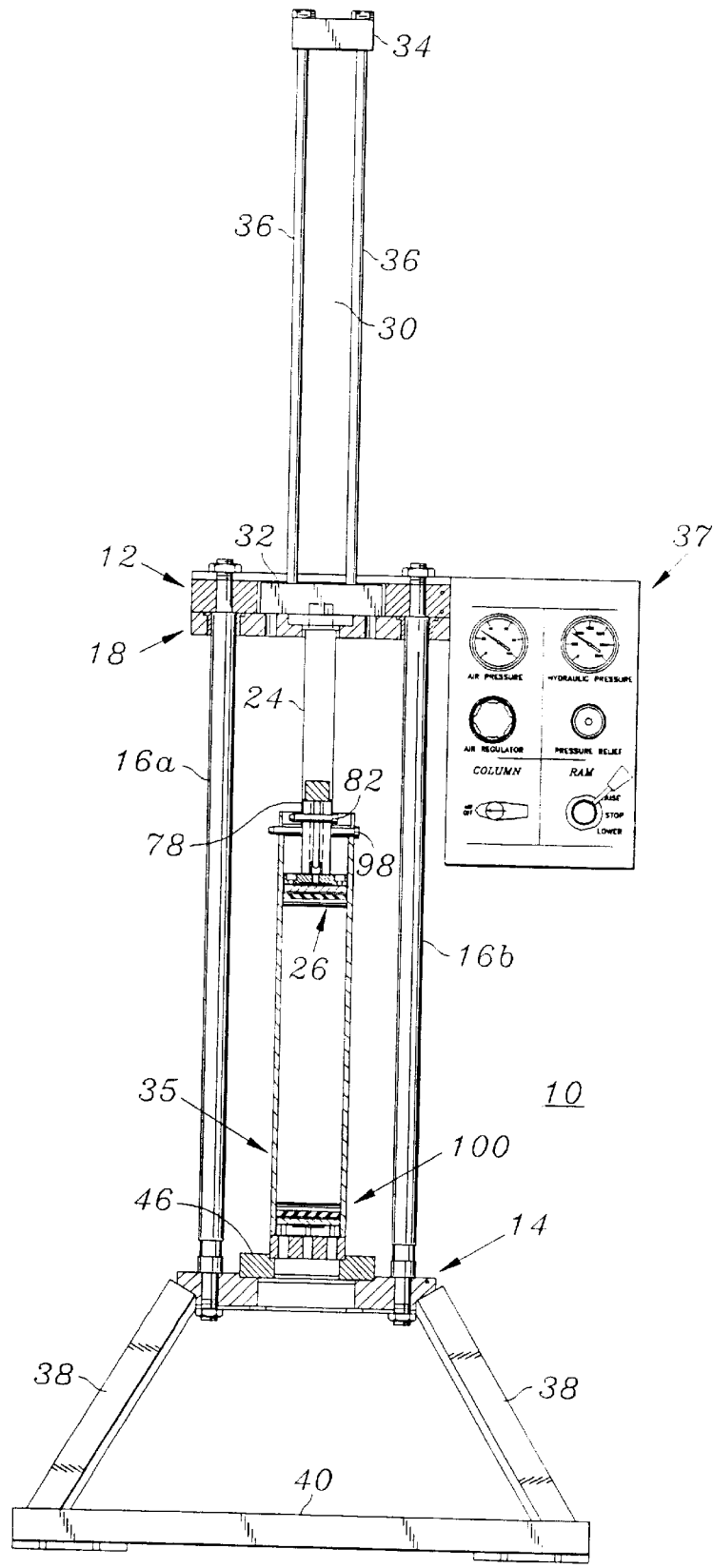
FIG. 5 is a side view partially in section of the apparatus of FIG. 4 showing the column tube after it has been driven downward onto the adaptor ring to receive the lower piston and lower end closure.

As shown in FIG. 3, the adaptor ring 46 of proper internal diameter is first secured to the top of the lower support plate 14 and an empty column tube 35 mounted thereon as shown. As depicted in FIG. 4, the compression rod and piston are then driven downwardly into an upper end of the empty column tube. Next, the compression rod and piston are releaseably secured to the column tube by a connector pin 98 passing through aligned holes 99 in the column tube and the piston coupler 78 as shown in FIG. 4. Upward movement of the compression rod and piston then lifts the column tube 35 from the adaptor 46 allowing a lower piston and bed support 100 including filters and fluid ports to be located on the adaptor ring as illustrated. Next, the compression rod and piston are lowered to lower the column tube 35 onto the bed support and lower piston 100 as depicted in FIG. 5. This is an important feature of the apparatus 10 of the present invention. Since the large diameter column tubes processed by the apparatus of the present invention are heavy even when empty and difficult to maneuver and position over lower pistons and bed supports. Furthermore, insertion of tightly fitting bed supports requires significant force. With the apparatus of the present invention however, all such lifting and positioning is accomplished by the hydraulic system of the compression mechanism 22.

Figure 6:
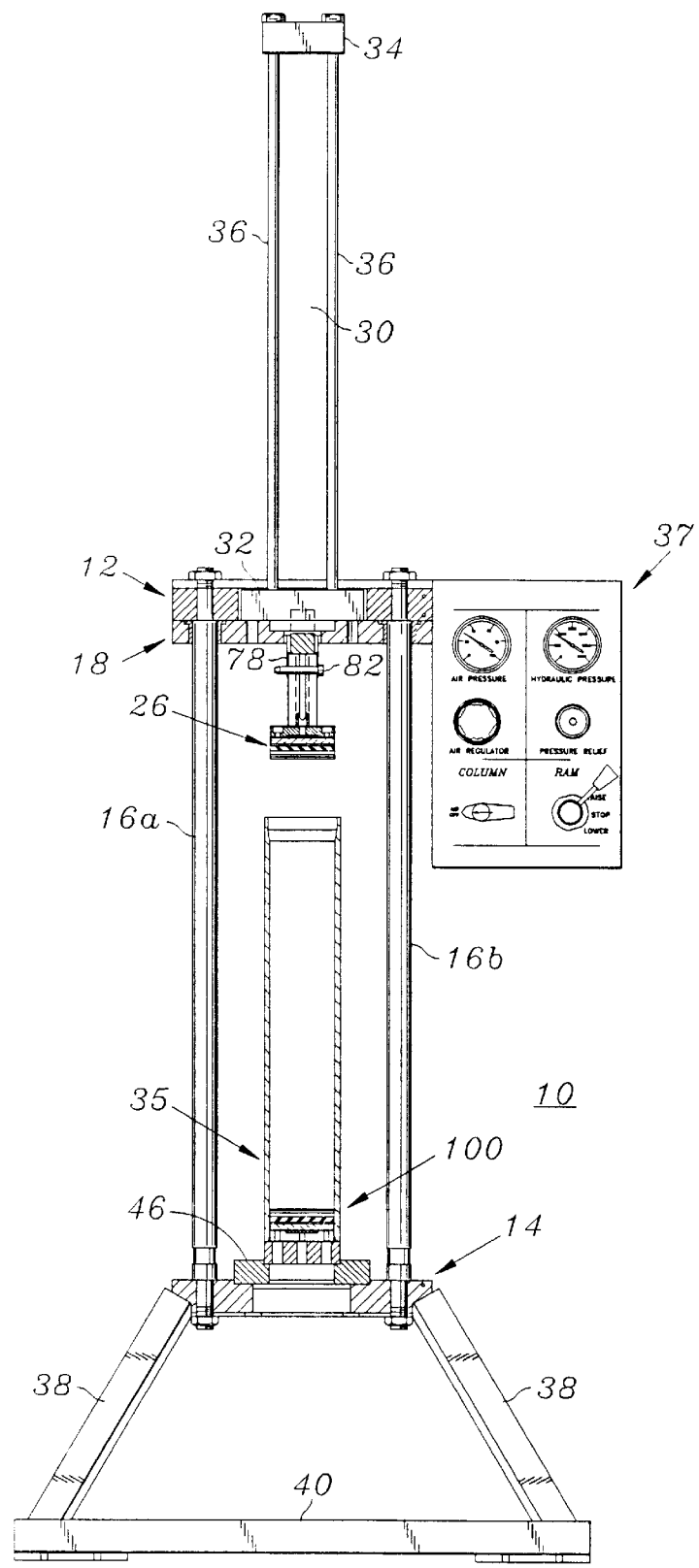
FIG. 6 is a side view partially in section of the apparatus of FIG. 5 after the connecting pin has been removed to release the compression piston and compression rod from the column tube, the compression rod and compression piston being depicted in a raised position with the upper end of the column tube open to receive a slurry of the packing material for packing upon a downward movement of the compression piston into the column tube.

Once the column tube 35 is seated on the lower piston and bed support 100 as depicted in FIG. 5, the connecting pin 98 is removed from the column tube 35 and coupler 78 and the compression rod and piston are allowed to move upwardly out of the upward end of the column tube to the position shown in FIG. 6. The upper open end of the column tube 35 is then clear to allow a pouring of a slurry of packing material into the column tube for compression by the compression piston 26 after an upper bed support is inserted into the column tube.

Thus, as described above the present invention overcomes the short comings of prior column packing apparatus by providing an apparatus which is vertically collapsible for packaging, shipment and relocation from one location to another in a laboratory. Also, the apparatus of the present invention provides for the lifting and positioning of empty column tubes and the positioning of lower pistons and bed supports therein without requiring operators to manually lift, locate and lower the column tubes. Further, the apparatus of the present invention is adapted to compact columns of different diameter by use of adaptor rings and compression pistons of different size which are readily mounted and removed from the apparatus which in packing operation repeatedly uses the same compression mechanism in the packing of such columns.

While a particular embodiment of the apparatus of the present has been described herein, changes and modifications in the illustrated embodiment may be made without departing from the spirit or scope of the present invention. For example, the apparatus may be inverted such that the compression mechanism is mounted below the column tube with the compression piston entering a lower open end of the tube to compress packing material as it is driven upward into the tube. Alternatively, the apparatus may be positioned horizontally rather than vertically. Accordingly, it is intended that the scope of the present invention be limited only by the terms of the following claims.

What is claimed is:

1. A method for compressing packing material in liquid chromatography column tubes of different diameter, comprising:

securing an adaptor ring to a lower support member over a bottom opening, the adaptor ring having an inner diameter adapted to receive a first column tube;

positioning the first column tube of a first diameter on the adapter ring over the bottom opening in the lower support member;

inserting a compression piston of a column packing compression mechanism vertically into an upper open end of the first column tube;

releaseably connecting the compression piston to the first column tube;

actuating the compression mechanism to raise the compression piston and lift the first column tube from the lower support member;

positioning a lower piston and column tube end closure on the adaptor ring;

actuating the compression mechanism to lower the compression piston and first column tube onto the end closure, lower piston and adaptor ring;

disconnecting the compression piston from the first column tube;

raising the compression piston from the upper end of the column tube whereby the first column tube is open to receive a slurry of a packing material;

positioning an upper end closure within the first column tube;

positioning the compression piston in the upper end of the first column tube; and driving the compression piston and upper end closure downward to compress the packing material within the first column tube.

2. The method of claim 1 further comprising:

releaseably connecting the compression piston to an upper end of the first column tube to lift the first column tube;

driving the compression piston upward to raise the first column tube from the lower support member;

releasing the compression piston from the first column tube to allow the first column tube to be removed from the apparatus;

replacing the compression piston with a new compression piston having a diameter matching the inner diameter of a second column tube to be packed by the apparatus;

replacing the adaptor ring with a new adapter ring having an inner diameter adapted to receive the second column tube;

positioning the second column tube on the new adapter ring;

lowering the new compression piston into an upper end of a second column tube;

releaseably connecting the new compression piston to the second column tube;

raising the new compression piston to lift a second column tube from the lower support member;

mounting a lower piston and lower end closure having outer matching the second column tube on the new adaptor ring;

lowering the new compression piston and second column tube onto the second end closure and second end piston; and releasing the new compression piston from the second column tube to allow a removal of the new compression piston therefrom and entry of a slurry of packing material into the second column tube for a compression by downward movement of the new compression piston within the second column tube.

* * * * *